US006221846B1

(12) United States Patent
Nishida et al.

(10) Patent No.: US 6,221,846 B1
(45) Date of Patent: Apr. 24, 2001

(54) OPHTHALMIC DRUG COMPOSITIONS

(75) Inventors: Teruo Nishida, 396-2, Nishikiwa, Ube-shi, Yamaguchi 755-0151; Katsuhiko Nakata, Sakurai; Masatsugu Nakamura, Nara, all of (JP)

(73) Assignees: Teruo Nishida, Ube; Santen Pharmaceuticals Co., Ltd., Osaka, both of (JP)

( * ) Notice: Subject to any disclaimer, the term of this patent is extended or adjusted under 35 U.S.C. 154(b) by 0 days.

(21) Appl. No.: 09/202,820

(22) PCT Filed: Jun. 11, 1997

(86) PCT No.: PCT/JP97/02015

§ 371 Date: Jul. 15, 1999

§ 102(e) Date: Jul. 15, 1999

(87) PCT Pub. No.: WO97/49419

PCT Pub. Date: Dec. 31, 1997

(30) Foreign Application Priority Data

Jun. 26, 1996 (JP) .................................... 8-165612

(51) Int. Cl.$^7$ .................................... A67K 38/00
(52) U.S. Cl. .................................... 514/15; 514/18; 514/912
(58) Field of Search ................... 514/15, 18, 912

(56) References Cited

U.S. PATENT DOCUMENTS

| 3,862,114 | 1/1975 | Scandrett . |
| 4,885,163 | 12/1989 | Shaar et al. . |
| 5,427,778 | 6/1995 | Finkenaur et al. . |
| 5,616,562 | 4/1997 | Murphy et al. . |

FOREIGN PATENT DOCUMENTS

| 0 176 436 | 4/1986 | (EP) . |
| 63-233925 | 9/1988 | (JP) . |
| 2-112 | 1/1990 | (JP) . |
| 5-25001 | 2/1993 | (JP) . |
| 6-48901 | 2/1994 | (JP) . |
| 7-500839 | 1/1995 | (JP) . |
| WO 92/22569 | 12/1992 | (WO) . |
| WO 93/08826 | 5/1993 | (WO) . |
| WO 95/13087 | 5/1995 | (WO) . |

OTHER PUBLICATIONS

Nakamura et al, "Effects of cytokines on type I collagen production in corneal fibroblasts", *Connective Tissue,* 27 (1), 65 (1995).

Nishida et al, "Clinical classification of the corneal epithelial disorders", *J. Clin. Opthalmol.,* 46, 738 (1992).

Chikako Katakami, "A New Treatment for Corneal Epithelial Defects using Fibronectin, EGF and Hyaluronic Acid", *Journal of Surgical Ophthalomology,* 5(4), 719–727 (1992).

Inoue et al, "The Sequential Changes of Substance P During Acute Herpetic Keratitis in Mice", *J. Jpn. Ophthalmol. Soc.,* 91, 982–987 (1987).

Toshio Katayama, "Ocular Inflammation and Neuropeptides in Rabbit Ocular Tissue", (1987), *J. Jpn. Ophthalmol. Soc.,* 92, 448–452 (1988).

Takasu et al, "Insulin–like Growth Factor I Stimulates Inositol Phosphate Accumulation, a Rise in Cytoplasmic Free Calcium, and Proliferation in Cultured Porcine Thyroid Cells", *Journal of Biological Chemistry,* 264 (31), 18485–18488 (1989).

Pedone et al, "Mono—and bi–allelic expression of insulin–-like growth factor II gene in human muscle tumors", *Human Molecular Genetics,* 3 (7), 1117–1121 (1994).

Nishida et al, "Fibronectin promotes epithelial migration of cultured rabbit cornea in situ", *Prog. Med.,* 13, 2627 (1993).

B.H. Rohde et al, "Effects of Some Opiates and Opioid Peptide Eyedrops on Melatonin Regulation in Rabbits", *Ophthalmic Research,* vol. 25, No. 6, pp. 378–385 (1993).

N.N. Osborne et al, "The Effect of Substance P and Other Tachykinins on Inositol Phospholipid Hydrolysis in Rabbit Retina, Superior Colliculus and Retinal Cultures", *Vision Research,* vol. 29, No. 7, pp. 757–764 (1989).

*Primary Examiner*—Zohreh Fay
(74) *Attorney, Agent, or Firm*—Frishauf, Holtz, Goodman, Langer & Chick, P.C.

(57) ABSTRACT

An ophthalmic composition for treating corneal disorder which comprises Phe-Gly-Leu-Met-NH$_2$ or a pharmaceutically acceptable salt thereof as an active ingredient. Also a composition for treating corneal disorders, particularly a composition for promoting corneal epithelial migration, which comprises Phe-Gly-Leu-Met-NH$_2$ or a pharmaceutically acceptable salt thereof and an insulin-like growth factor I. Preferably the compositions are in the form of ophthalmic formulations.

14 Claims, No Drawings

# OPHTHALMIC DRUG COMPOSITIONS

TECHNICAL FIELD

The present invention relates to an ophthalmic drug composition containing Phe-Gly-Leu-Met-NH$_2$ (hereinafter, referred to as FGLM), which is a tetrapeptide at the C-terminal of Substance P, or a pharmaceutically acceptable salt thereof as an active ingredient. More particularly, it relates to a therapeutic agent for corneal disorders having a promoting action on corneal epithelial wound healing, characterized in that an insulin-like growth factor I (hereinafter, referred to as IGF-I), which is one of the growth factors, is formulated as another active ingredient with FGLM in a preparation or these two are administered jointly.

BACKGROUND ART

The cornea is a transparent, avascular tissue having a diameter of about 1 cm and a thickness of about 1 mm. Transparency of the cornea affects visual functions greatly and various physiological and biochemical phenomena in the cornea function mainly with an object of maintenance of transparency of the cornea.

Corneal epithelial defects caused by various diseases such as corneal ulcer, corneal erosion, keratitis and dry eye heals spontaneously unless mixed infection intercurrently occurs. However, if the healing is delayed or does not occur due to some causes and the corneal defects become persistent, the normal construction of the epithelium is badly affected, and further even the structure and function of corneal stroma and endothelium are damaged. The principle of the conventional therapeutic methods is merely passive, i.e., the surface of the cornea is protected from outside stimulation whereby the epithelium is spontaneously extended to re-cover the defected area. Recent progress of cell biology has revealed factors participating in proliferation, migration, attachment, spreading of cells, etc. and it was reported that compounds which enhance the migration of corneal epithelium play an important role in healing the corneal epithelial defects (*Jpn. J. Clin. Ophthalmol.*, 46, 738–743 (1992); and *Jpn. J. Ophthalm. Surg.*, 5, 719–727 (1992)).

FGLM is a tetrapeptide at the C-terminal of Substance P which is disclosed in U.S. Pat. No. 3,862,114 and the patent describes that it has an hypotensive action. Substance P is a polypeptide consisting of eleven amino acids which show actions such as vasodilation, smooth muscle contraction, promotion of salivary gland secretion and diuresis. With regard to Substance P, various studies were conducted in an ophthalmic field. For example, improvement in aberrant conjunctival goblet cell secretion in ophthalmic diseases was disclosed (WO95/13087) and sequential charges of Substance P in inflammation such as keratitis was reported (*J. Jpn. Ophthalmol. Soc.*, 91, 982–987 (1987); ibid., 92, 448–452 (1988)). However, there has been no report on FGLM, which is its partial peptide, in an ophthalmic field.

On the other hand, an insulin-like growth factor is one of the growth factors controlling the growth of normal human cells such as epidermal growth factor, fibroblast growth factor, platelet-derived growth factor and transforming growth factor, and there are IGF-I and an insulin-like growth factor II (hereinafter, referred to as IGF-II) therein. Recently, it was reported that IGF-I stimulates thyroid cell proliferation (*J. Biol. Chem.*, 264, 18485–18488 (1989)), that IGF-II regulates muscle growth and differentiation (*Hum. Mol. Genet.*, 3, 1117–1121 (1994)), etc. In an ophthalmic field, also, it was disclosed that IGF-I, IGF-II and functional derivatives thereof promote the survival of retinal neurons (cf. Japanese Laid-Open Patent Publication Hei-07/500, 839), that IGF-II is effective for therapy of every wound of various areas including the wound upon corneal transplantation (Japanese Laid-Open Patent Publication Sho-63/233, 925) and that ocular tissues such as cornea provided to transplantation can be preserved at low temperature in a fresh state of the tissues by using a solution containing the above-mentioned growth factor (Japanese Laid-Open Patent Publications Hei-05/025,001 and Hei-06/048,901). It was also disclosed that, in general, gel compositions containing the growth factor are effective for wound healing in anterior segments etc. (Japanese Laid-Open Patent Publication Hei-02/000,112). However, the growth factors which are specifically disclosed in those patent publications are epidermal growth factors only and there is no description on the effect of IGF-I.

IGF-II has been known to be useful for a therapy of wound upon corneal transplantation etc. as mentioned above. However, with regard to IGF-I, there is only a report that it does not affect corneal epithelial wound healing (*Connect. Tissue*, 27, 65 (1995)).

It was reported that Substance P itself does not affect the corneal epithelial wound healing but it promotes the corneal epithelial wound healing when it coexists with epidermal growth factor out of growth factor (*Prog. Med.*, 13, 2626–2627 (1993)) or IGF-I (*Connect. Tissue*, 27, 65 (1995)). However, it has not been revealed that which site of Substance P is an activity-exhibiting site.

As mentioned above, it has been a very interesting subject to find a minimum activity-exhibiting site of Substance P and to study actions of the compound in such a minimum unit in an ophthalmic field, particularly to study the action on corneal disorders.

DISCLOSURE OF THE INVENTION

The present inventors have paid their attention to the partial peptide at the C terminal of Substance P and studied its action on corneal disorders. As a result, they have found that FGLM, which is a tetrapeptide at the C terminal of Substance P, promotes the corneal epithelial wound healing when it coexists with IGF-I and that FGLM is a minimum unit of the partial peptide of Substance P for exhibiting the above-mentioned action. Thus, the novel use of FGLM as an ophthalmic drug composition has been found. Further, it has been found that a combined use of FGLM or a pharmaceutically acceptable salt thereof together with IGF-I as another active ingredient is useful for therapy of corneal disorders such as corneal ulcer, corneal erosion, keratitis and dry eye, where the cornea is in a wounded state due to various causes.

FGLM is a tetrapeptide of the C terminal of Substance P and has a structure of Phe-Gly-Leu-Met-NH$_2$. Phe, Leu and Met have L-, D- and DL-forms respectively and all of them belong to the present invention. The preferred embodiment is a compound where all of them are the L-form.

Examples of the pharmaceutically acceptable salt of FGLM are hydrochloride, sulfate, phosphate, lactate, maleate, fumarate, oxalate, methanesulfonate and p-toluenesulfonate.

The term "corneal disorders" used in the present invention stands for corneal ulcer, corneal erosion, keratitis, dry eye and the like, where the cornea is in a wounded state due to various causes.

In order to study the usefulness of FGLM and IGF-I, their influence on corneal disorders has been investigated. Although the details will be mentioned later in the item of the "pharmacological tests", it has been found that the coexistence of FGLM and IGF-I promotes the migration of corneal epithelium in a tissue culture system of cornea pieces and the wound healing after corneal erosion. From these findings, it has been revealed that FGLM and IGF-I are useful for the therapy of corneal disorders such as corneal ulcer, corneal erosion, keratitis and dry eye, where the cornea is in a wounded state due to various causes and that they are particularly useful for the therapy of corneal erosion and dry eye.

FGLM or a pharmaceutically acceptable salt thereof and IGF-I can be administered either orally or parenterally and these two active ingredients can be either formulated together in one preparation or formulated separately, followed by administering them together. Examples of the dosage form are tablets, capsules, granules, powder, injection and ophthalmic preparations and the ophthalmic preparations such as eye drops and an eye ointment is particularly preferable. They can be prepared by widely used techniques. In the case of oral preparations such as tablets, capsules, granules and powder, fillers such as lactose, crystalline cellulose, starch and vegetable oil, lubricants such as magnesium stearate and talc, binders such as hydroxypropyl cellulose and polyvinylpyrrolidone, disintegrator such as calcium carboxymethyl cellulose and lowly substituted hydroxypropylmethyl cellulose, coating agents such as hydroxypropylmethyl cellulose, Macrogol and silicone resin, film forming agents such as gelatin and the like can be added thereto, if necessary. In the case of eye drops, isotonic agents such as sodium chloride, buffers such as sodium phosphate, preservatives such as benzalkonium chloride and the like can be used. The pH can be within a range that is acceptable in the ophthalmic preparations and, preferably, it is within a range of 4–8. In the case of eye ointment, widely used bases such as white vaseline and liquid paraffin can be used for the preparation.

The dose can be appropriately selected depending upon symptom, age, dosage form, etc. Thus, in the case of oral preparations, the doses of FGLM or pharmaceutically acceptable salt thereof and IGF-I are usually 0.1–5,000 mg (as FGLM) and 0.001–100 mg per day, respectively, preferably 1–1,000 mg (as FGLM) and 0.01–10 mg per day, respectively. Administration can be conducted by instillating it once or several times a day. In the case of ophthalmic preparations, concentrations of those active ingredients are 0.001–109 (w/v) (as FGLM) and 0.00001–0.1% (w/v), respectively, preferably 0.01–1% (w/v) (as FGLM) and 0.0001–0.01% (w/v), respectively. Administration can be conducted by instillating it once or several times a day.

Examples of the preparations and the results of pharmacological tests are given as hereunder although they are intended to give better understanding of the present invention and they do not limit the scope of the present invention.

Best Mode for Carrying Out the Invention

Examples of the Preparations

Representative examples of the preparations used in the present invention will be given hereunder.

1. Ophthalmic Preparations

The ophthalmic preparations having the following formulations were prepared by widely used methods.

| Formulation Example 1. (Eye Drops) (in 100 ml) | |
|---|---|
| FGLM | 100 mg |
| Sodium chloride | 900 mg |
| Sodium hydroxide | q.s. |
| Hydrochloric acid | q.s. |
| Sterile purified water | q.s. |

Eye drops containing 1 mg, 5 mg, 10 mg, 50 mg, 500 mg and 1,000 mg of FGLM in 100 ml can be prepared as well in the same manner as in Formulation Example 1.

| Formulation Example 2. (Eye Drops) (in 100 ml) | |
|---|---|
| IGF-I | 1 mg |
| Sodium chloride | 900 mg |
| Sodium hydroxide | q.s. |
| Hydrochloric acid | q.s. |
| Sterile purified water | q.s. |

Eye drops containing 0.01 mg, 0.05 mg, 0.1 mg, 0.5 mg, 5 mg, 10 mg, 50 mg and 100 mg of IGF-I in 100 ml can be prepared as well in the same manner as in Formulation Example 2.

| Formulation Example 3 (Eye Drops) (in 100 ml) | |
|---|---|
| FGLM | 100 mg |
| IGF-I | 1 mg |
| Sodium chloride | 900 mg |
| Sodium hydroxide | q.s. |
| Hydrochloric acid | q.s. |
| Sterile purified water | q.s. |

Eye drops containing 1 mg, 5 mg, 10 mg, 50 mg, 500 mg and 1,000 mg of FGLM and 0.01 mg, 0.05 mg, 0.1 mg, 0.5 mg, 10 mg, 50 mg and 100 mg of IGF-I in any combination thereof can be prepared as well in the same manner as in Formulation Example 3.

| Formulation Example 4. (Eye Ointment) (in 100 g) | |
|---|---|
| FGLM | 100 mg |
| IGF-I | 1 mg |
| White vaseline | 90 g |
| Liquid paraffin | q.s |

Eye ointments containing 1 mg, 5 mg, 10 mg, 50 mg, 100 mg, 500 mg and 1,000 mg of FGLM and 0.01 mg, 0.05 mg, 0.1 mg, 0.5 mg, 1 mg, 10 mg, 50 mg and 100 mg of IGF-I in any combination thereof can be prepared as well in the same manner as in Formulation Example 4.

2. Tablets

Tablets of the following formulations were prepared by widely used methods.

| Formulation Example 5. (in 100 mg) | |
| --- | --- |
| FGLM | 10 mg |
| Lactose | 59.4 mg |
| Corn starch | 20 mg |
| Calcium carboxymethyl cellulose | 6 mg |
| Hydroxypropyl cellulose | 4 mg |
| Magnesium stearate | 0.6 mg |

The tablet of the above formulation can be coated with 2 mg of a coating agent such as hydroxypropyl cellulose.

Tablets containing 0.1 mg, 0.5 mg, 1 mg, 5 mg and 50 mg of FGLM in 100 mg of a tablet can be prepared as well in the same manner as in Formulation Example 5.

| Formulation Example 6. (in 100 mg) | |
| --- | --- |
| IGF-I | 0.1 mg |
| Lactose | 69.3 mg |
| Corn starch | 20 mg |
| Calcium carboxymethyl cellulose | 6 mg |
| Hydroxypropyl cellulose | 4 mg |
| Magnesium stearate | 0.6 mg |

The tablet of the above formulation can be coated with 2 mg of a coating agent such as hydroxypropyl cellulose.

Tablets containing 0.001 mg, 0.01 mg, 0.05 mg, 0.5 mg, 1 mg, 5 mg, 10 mg and 50 mg of IGF-I in 100 mg of a tablet can be prepared as well in the same manner as in Formulation Example 6.

| Formulation Example 7. (in 100 mg) | |
| --- | --- |
| FGLM | 10 mg |
| IGF-I | 0.1 mg |
| Lactose | 59.3 mg |
| Corn starch | 20 mg |
| Calcium carboxymethyl cellulose | 6 mg |
| Hydroxypropyl cellulose | 4 mg |
| Magnesium stearate | 0.6 mg |

The tablet of the above formulation can be coated with 2 mg of a coating agent such as hydroxypropyl cellulose.

Tablets containing 0.1 mg, 0.5 mg, 1 mg, 5 mg and 10 mg of FGLM and 0.001 mg, 0.01 mg, 0.05 mg, 0.1 mg, 0.5 mg, 1 mg, 5 mg and 10 mg of IGF-I in 100 mg of a tablet in any combination thereof can be prepared as well in the same manner as in Formulation Example 7.

Pharmacological Tests

1) Corneal Epithelial Migration (in vitro) The cornea of male Japanese white rabbits was used. The influence on migration of corneal epithelium was investigated using as an index the extended length of cornea epithelium in a tissue culture system of the cornea pieces according to a method of Nishida et al (J. Cell Biol., 97, 1653–1657 (1983)).

(Experimental Method)

Cornea blocks (six blocks per group) cut out from cornea pieces of the rabbit were incubated in a culture medium (TC-199) containing the test compound under the condition of 37° C. and 5% of $CO_2$ for 24 hours. After the incubation, the cornea blocks were fixed in a mixed solution of ethanol and glacial acetic acid (95:5 by volume) and embedded in paraffin to prepare the slices. Paraffin was removed from the slices, then the slices were stained with hematoxyline and eosin and the extended length of the epithelial cell layer was measured under a microscope.

The product which was prepared by the same incubation using a culture medium containing no test compound was used as a control.

(Results)

As an example of the results of the experiment, Table 1 shows the result where incubation was conducted using a culture medium containing FGLM alone, IGF-I alone and both FGLM and IGF-I. Table 2 shows the result where the peptide which was added to the culture medium was Gly-Leu-Met-$NH_2$ (hereinafter, referred to as GLM), FGLM, Val-Gly-Leu-Met-$NH_2$ (hereinafter, referred to as VGLM), Ile-Gly-Leu-Met-$NH_2$ (hereinafter, referred to as IGLM), Tyr-Gly-Leu-Met-$NH_2$ (hereinafter, referred to as YGLM) or Phe-Phe-Gly-Leu-Met-$NH_2$ (hereinafter, referred to as FFGLM).

TABLE 1

| | Extended Length ($\mu$m) |
| --- | --- |
| Control | 433 |
| FGLM (20 $\mu$M) | 426 |
| IGF-I (10 ng/ml) | 430 |
| FGLM (20 $\mu$M) and IGF-I (10 ng/ml) | 662 |

TABLE 2

| | Extended Length ($\mu$m) |
| --- | --- |
| Control | 433 |
| IGF-I (10 ng/ml) | 430 |
| IGF-I (10 ng/ml) and GLM (20 $\mu$M) | 445 |
| IGF-I (10 ng/ml) and FGLM (20 $\mu$M) | 662 |
| IGF-I (10 ng/ml) and VGLM (20 $\mu$M) | 440 |
| IGF-I (10 ng/ml) and IGLM (20 $\mu$M) | 426 |
| IGF-I (10 ng/ml) and YGLM (20 $\mu$M) | 433 |
| IGF-I (10 ng/ml) and FFGLM (20 $\mu$M) | 655 |

As shown in Table 1, while no influence on migration of corneal epithelium was noted by a sole administration of FGLM or of IGF-I, when incubation was conducted in a culture medium containing both FGLM and IGF-I, a remarkable promotion of the migration of corneal epithelium was noted.

Further, as shown in Table 2, with regard to the peptide which was added to the culture medium together with IGF-I, while a remarkable promotion of the migration of corneal epithelium was noted when FGLM or FFGLM was used, no influence on the migration of corneal epithelium was noted when the C-terminal tripeptide of Substance P or a peptide similar to FGLM was added. 2) Promoting Action on Corneal Wound Healing (in vivo)

Male Japanese white rabbits were used. Corneal erosion was caused according to a method of Cintron et al (*Ophthalmic Res.*, 11, 90–96 (1979)). The wounded area was measured using an area stained with fluorescein as an index and the influence on the corneal wound healing was investigated.

(Experimental Method)

After the onset of corneal erosion, eye drops containing the test compound were instilled every two hours six times a day (50 μl per administration). In measuring the wounded area, a fluorescein staining was conducted and photographs of the cornea were taken and measured. The area of the cornea stained with fluorescein in the photographs was calculated by means of an image analysis processing system.

A rabbit to which a base containing no test compound was instilled was used as a control.

(Results)

As an example of the results of the experiment, Table 3 shows wounded areas of immediately after the onset of corneal erosion and 12, 24, 36 and 48 hours thereafter upon the treatment where eye drops containing 0.05% (w/v) of FGLM (F-3) alone was instilled; where eye drops containing 0.0001% (w/v) of IGF-I (I6) alone was instilled; and where both eye drops containing 0.05% (w/v) of FGLM (F-3) and that containing 0.0001% (w/v) of IGF-I (I-6) were instilled.

TABLE 3

| | Wounded Area ($mm^2$) after Corneal Erosion | | | | |
|---|---|---|---|---|---|
| | 0 hr | 12 hrs | 24 hrs | 36 hrs | 48 hrs |
| Control | 35.4 | 31.6 | 20.6 | 11.7 | 3.3 |
| FGLM | 35.4 | 31.0 | 19.9 | 10.9 | 2.9 |
| IGF-I | 35.5 | 30.3 | 19.0 | 10.0 | 2.6 |
| FGLM + IGF-I | 35.5 | 28.1 | 10.5 | 2.4 | 0.1 |

As shown in Table 3, while no influence was noted on wound healing after corneal erosion by a sole administration of FGLM or IGF-I, when both FGLM and IGF-I were instilled, a remarkable promotion was noted in wound healing.

From the above-mentioned pharmacological tests, it has been found that, when FGLM, which is one of the partial peptides of Substance P, or a pharmaceutically acceptable salt thereof coexists with IGF-I, which is one of the growth factors, the former exhibits an promoting action on the corneal epithelimal wound healing whereby it is useful as a therapeutic agent for corneal disorders where the cornea is wounded due to various causes such as corneal ulcer, corneal erosion, keratitis and dry eye.

In addition, while the promoting action on the corneal epithelial migration was noted in a tetrapeptide or a pentapeptide at the C-terminal of Substance P when it coexists with IGF-I, this action was not noted in a tripeptide at the C-terminal of Substance P. Accordingly, it has been now revealed that the minimum unit of the partial peptide of Substance P coexisting with IGF-I, which is necessary for exhibiting the promoting action on corneal epithelial wound healing, was the tetrepeptide at the C-terminal. Further, when the amino acid at the N-terminal of the tetrapeptide was other than Phe, no promoting action on the corneal epithelial migration was noted. Accordingly, it has been revealed that the tetrapeptide coexisting with IGF-I which is necessary for exhibiting the promoting action on corneal epithelial wound healing should be FGLM, which is a tetrapeptide at the C-terminal of Substance P.

What is claimed is:

1. A composition for treating a corneal disorder comprising a pharmaceutically effective amount of Phe-Gly-Leu-Met-$NH_2$ or a pharmaceutically acceptable salt thereof and a pharmaceutically effective amount of an insulin-like growth factor I, as active ingredients, and optionally a pharmaceutically acceptable carrier.

2. The composition according to claim 1, wherein the corneal disorder is a corneal ulcer, corneal erosion, keratitis or dry eye.

3. The composition according to claim 1, wherein the corneal disorder is corneal erosion or dry eye.

4. The composition according to claims 1, 2 or 3, wherein the composition is in a dosage form which is an ophthalmic preparation.

5. A composition for promoting corneal epithelial migration comprising a pharmaceutically effective amount of Phe-Gly-Leu-Met-$NH_2$ or a pharmaceutically acceptable salt thereof and a pharmaceutically effective amount of an insulin-like growth factor I, as active ingredients, and optionally a pharmaceutically acceptable carrier.

6. The composition according to claim 5, wherein the composition is in a dosage form which is an ophthalmic preparation.

7. The composition of claim 1, wherein the composition is in the form of an ophthalmic formulation, the Phe-Gly-Leu-Met-$NH_2$ is in a concentration of 0.001 to 10% (w/v) and the insulin-like growth factor is in a concentration of 0.00001 to 0.1% (w/v).

8. The composition of claim 1, wherein the Phe-Gly-Leu-Met-$NH_2$ is in a concentration of 0.01 to 1 (w/v) and the insulin-like growth factor is in a concentration of 0.0001 to 0.01% (w/v).

9. A method for treating a corneal disorder comprising administering to a patient in need thereof a composition comprising a pharmaceutically effective amount of Phe-Gly-Leu-Met-$NH_2$ or a pharmaceutically acceptable salt thereof, either alone or in combination with a pharmaceutically acceptable carrier.

10. The method of claim 9, wherein the composition further comprises a pharmaceutically effective amount of an insulin-like growth factor I.

11. The method of claim 10, wherein the corneal disorder is a corneal ulcer, corneal erosion, keratitis or dry eye.

12. The method of claim 10, wherein corneal epithelial migration is promoted.

13. The method of claim 11, wherein the composition is in the form of an ophthalmic formulation, the Phe-Gly-Leu-Met-$NH_2$ is in a concentration of 0.001 to 10% (w/v) and the insulin-like growth factor is in a concentration of 0.00001 to 0.1% (w/v).

14. The method of claim 13, wherein the Phe-Gly-Leu-Met-$NH_2$ is in a concentration of 0.01 to 1% (w/v) and the insulin-like growth factor is in a concentration of 0.0001 to 0.01% (w/v).

* * * * *